US00PP13624P2

(12) United States Plant Patent
Vardi et al.

(10) Patent No.: US PP13,624 P2
(45) Date of Patent: Mar. 4, 2003

(54) CITRUS TREE NAMED 'NECTAR'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL)

(73) Assignee: State of Israel-Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,478

(22) Filed: Nov. 20, 2000

(51) Int. Cl.[7] ..... A01H 5/00
(52) U.S. Cl. ..... Plt./202

(58) Field of Search ..... Plt./202

(56) References Cited

PUBLICATIONS

GTITM UPOVROM Citation for 'Nectar' as per IL PBR 01875; Feb. 26, 1999.*

* cited by examiner

*Primary Examiner*—Kent L. Bell
(74) *Attorney, Agent, or Firm*—Akerman Senterfitt

(57) ABSTRACT

A new variety of mandarin citrus is described that is distinguished by fruit having no seeds and flowers having anthers bearing sterile pollen.

2 Drawing Sheets

FIELD OF THE INVENTION

A new mandarin citrus tree *Citrus reticulata* hybrid is described. The new variety named 'Nectar' is desirable to the consumer because it has seedless fruit and to the commercial grower because it bears late ripening (end of December to beginning of February) citrus fruits having rich having rich flavor.

BACKGROUND OF THE NEW TREE

The present invention relates to a new and distinct variety of mandarin tree *Citrus reticulata* hybrid developed by inventors Aliza Vardi, Pinchas Spiegel-Roy, Avraham Elchanati and Ahuva Frydman-Shani from a controlled pollination made at the Volcani Center in Bet Dagan, Israel.

Asexual reproduction by conventional bud grafting onto Troyer reetstock nucellar seedlings of the new variety in Israel has shown that the new characteristics are stabilized and permanently fixed through successive propagation.

The objective in breeding the present new tree variety, assigned the denomination 'Nectar' was to obtain a late ripening citrus mandarin having fruit with few or no seeds. In the spring of 1979, a controlled pollination cross of 'Wilking' (unpatented) mandarin (*Citrus reticulata* Blanco) was made at the Agricultural Research Organization, The Volcani Center, in Bet Dagan, Israel. The fruit was collected in November 1979 and seeds of the fruits were extracted and subsequently germinated during January 1980. About 150 seedlings were grown from the germinated seeds. Each seedling was grafted in September 1982 onto Troyer rootstock nucellar seedlings. The grafted plants were planted in June, 1984 in the Agricultural Research Organization experimental grove, Bet Dagan, Israel. The first fruits were observed in January 1988 and observations of the fruits were again made in 1989. One of the 140 seedlings was designated 56/4. This scion was observed to be fully ripe in the last week in December to the end of January. The fruit of this selection was orange in color and completely seedless.

Bud wood was taken from 56/4 and grafted in the spring of 1988 onto 6 Troyer rootstock. The grafted plants were planted a year later in the experimental grove of the Agricultural Research Organization in Bet Dagan. The first crop of trees was obtained in 1992. The yield of the scion grafted onto Troyer rootstock was good. The fruit was fully ripe in January. The color of the ripe fruit was orange and the fruit was easy to peel and had a very rich flavor. The juice had a sugar concentration of about 13% and an acid concentration of about 0.9%.

SUMMARY OF THE INVENTION

Some characteristics of the new mandarin tree, designated 'Nectar', were compared with its seed and pollen parent 'Wilking', as shown in Table 1.

TABLE 1

| Tree | Fruit color | Chromosone Number | Seeds/fruit | Pollen fertility[1] |
|---|---|---|---|---|
| 'Nectar' | Orange RHS 24A | 2n = 18 | 0 | Sterile 0% |
| 'Wilking' | Orange RHS 24A | 2n = 18 | 6–15 | 94% |

[1]Estimated by acetocarmine staining

The following is a detailed description of the new mandarin citrus variety based on observations made under typical Israeli grove conditions. Observations were made on 5–6 year old trees in Israel.

The tree is medium sized, about 3 to 4 meters high by 4 meters wide at 5–6 years after planting. This is quite similar to 'Wilking'. The tree's vigor is also medium with an annual terminal growth after pruning of about 100–110 cm in length and 10–12 mm in diameter as measured in 1993 in Bet Dagan, Israel. Young shoots have no anthocyanin coloration at the tip.

The tree is quite productive with a slight tendency to alternate bearing. The canopy is moderately dense. The bark of the young shoots is initially smooth and green gradually turning into a smooth grayed-green.

The chromosome number of the tree is diploid (2n=18) as is the chromosome number of the parents.

The leaves somewhat resemble that of 'Wilking' in shape and size. Foliar flushes, as measured in Bet Dagan, Israel, occur between April and September. The color and veination of the leaves are quite similar to that of 'Wilking'. Leaf blade is quite firm and straight in cross section. Petioles are without wings.

Flowering, as measured in Bet Dagan, Israel, in 1993 occurs between mid March and the beginning of April. The characteristics of the flowering and the flower parts are similar to 'Wilking' with one exception: the anthers contain aborted pollen only. Terminal flower buds have no anthocyanin coloration. Anther color is yellow with 0–1% stainable pollen grain as obtained by staining with acetocarmine. The trees flower once per year.

The fruit is seedless. The fruit shape is somewhat flat and it is medium sized. When 50 fruits were measured, the fruit had an average weight of 98 grams, an average height 46 mm, and an average diameter 68 mm. The fruit surface is usually smooth with an orange color, 24A, on The Royal Horticultural Society of London Colour Chart, and bears an average number of conspicuous rind oil glands. Fruit ripening does not differ from outside of the canopy to the inside, but the fruit color of the outside canopy is a little brighter as compare to the fruit color of the inside canopy. There is no persistence of the style and the areola is not completely developed. A navel is absent or very rare. The rind is thin and easy to peel. Fruit productivity of a single tree at age 7 is about 40 kg.

The color of the albedo is yellow-orange and the flesh is orange in color. The fruit contains 10–11 segments and is very juicy. The fruit reaches maturity in January in Israel. The ripening of the fruit on the tree and within the fruit is uniform. Fruit remaining on the tree does not regreen and does begin to lose quality until mid February. The fruit has attractive appearance and the fruit flavor is very rich and pleasant.

DESCRIPTION OF THE PHOTOGRAPHS

The new citrus tree is illustrated in the accompanying color photographs.

Sheet one depicts the whole tree and canopy shape of the new variety.

Sheet two shows the exterior of the fruit as well as transverse midsections in a plane substantially perpendicular to the axis, illustrating no seeds.

DESCRIPTION OF THE NEW TREE

The following is a detailed description of the new mandarin citrus variety based on observations made under typical Israeli grove conditions. Color designations have been determined from The R.H.S. Colour Chart published by The Royal Horticultural Society, London.

Tree:

*Origin.*—Self-pollination cross of 'Wilking' mandarin.

*Classification.*—Botanical: *Citrus reticulata* hybrid. Common: Mandarin citrus. Cultivar: 'Nectar'.

*Shape.*—Round with tendency to be upright with growth of young shoots.

*Thorns.*—Appear only at the juvenile stage; at the productive stage is thornless.

*Branching.*—Upright.

*Canopy.*—Moderately dense.

*Trunk.*—39 cm at 20 cm above the ground.

*Bark.*—Immature: Smooth, yellow-green, RHS 146B. Mature: Smooth, grayed-green, RHS 189A.

*Leaf.*—Size: Length: 92 mm, width 34.0 mm. Shape: Lanceolate and taper pointed. Leaf blade: Firm, straight in cross section. Petioles: Wingless, 12 mm length, 1.5 mm in diameter, Green RHS 147B. Foliar flushes: April-September (Israel). Color: Green RHS 147A (upper), Green RHS 147B (lower).

*Habit.*—Medium vigor.

Height.—3–4 m (5–6 years).

*Width.*—4 m (5–6 years).

*Disease resistance.*—No particular susceptibility or resistance observed.

*Winter hardiness.*—Winter temperature in Bet Dagan, Israel averages 4–7 degrees Centigrade.

Flower:

*Petals.*—5.

*Petal color.*—White RHS 155D (upper and lower).

*Flowering period.*—Mid March-beginning of April in Bet Dagan, Israel.

*Flower drop.*—April.

*Stamens.*—20, complete style.

*Anther color.*—Yellow RHS 9D.

*Pollen fertility.*—Aborted pollen only.

*Anthocyanina coloration.*—None.

Fruit:

*Shape.*—Slight oblate.

*Size.*—Medium.

*Weight.*—98 g (average of 50 fruits).

*Height.*—46 mm.

*Diameter.*—68 mm.

*Skin color.*—Orange, RHS 24A.

*Rind oil gland.*—Conspicuous, average number (48/$cm^2$).

*Style.*—No persistence.

*Navel.*—Absent.

*Rind.*—Thin (2–3 mm) and easy to peel.

*Albedo.*—Yellow-orange RHS 19B.

*Flesh color.*—Orange RHS 25A.

*Areola.*—Incompletely developed.

*Fruit segments.*—10–11.

*Time of maturity.*—Date of picking_January (Israel).

*Fruit extract.*—(Test conducted Jan. 16, 1997). Total soluble solids (TSS): 13%. Acid content: 0.9%. TSS/acid ratio 14.4. Flavor: Rich flavor.

Seeds: None.

What is claimed is:

1. A new and distinct variety of *Citrus reticulata* hybrid tree substantially as herein described and shown.

* * * * *

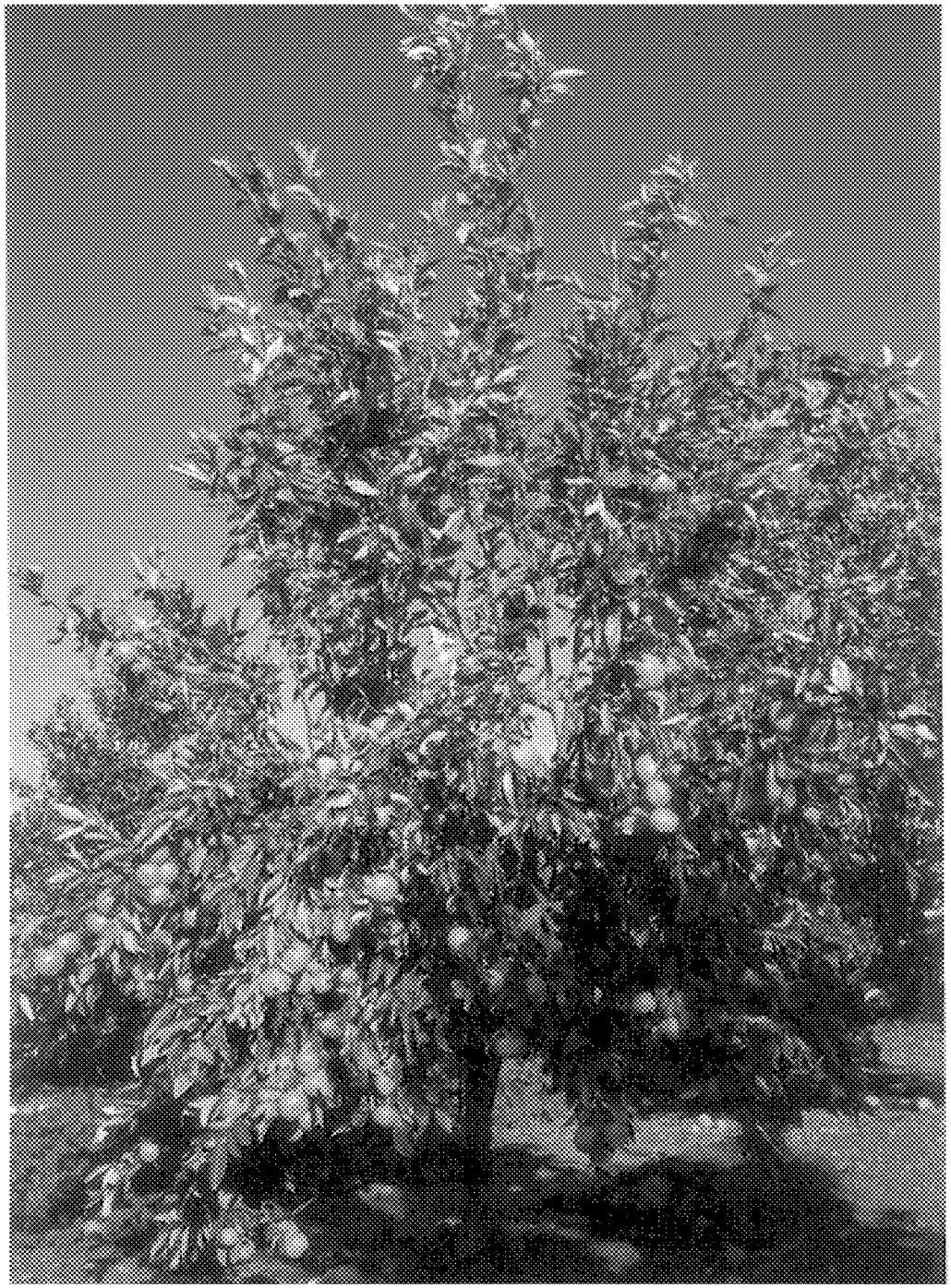

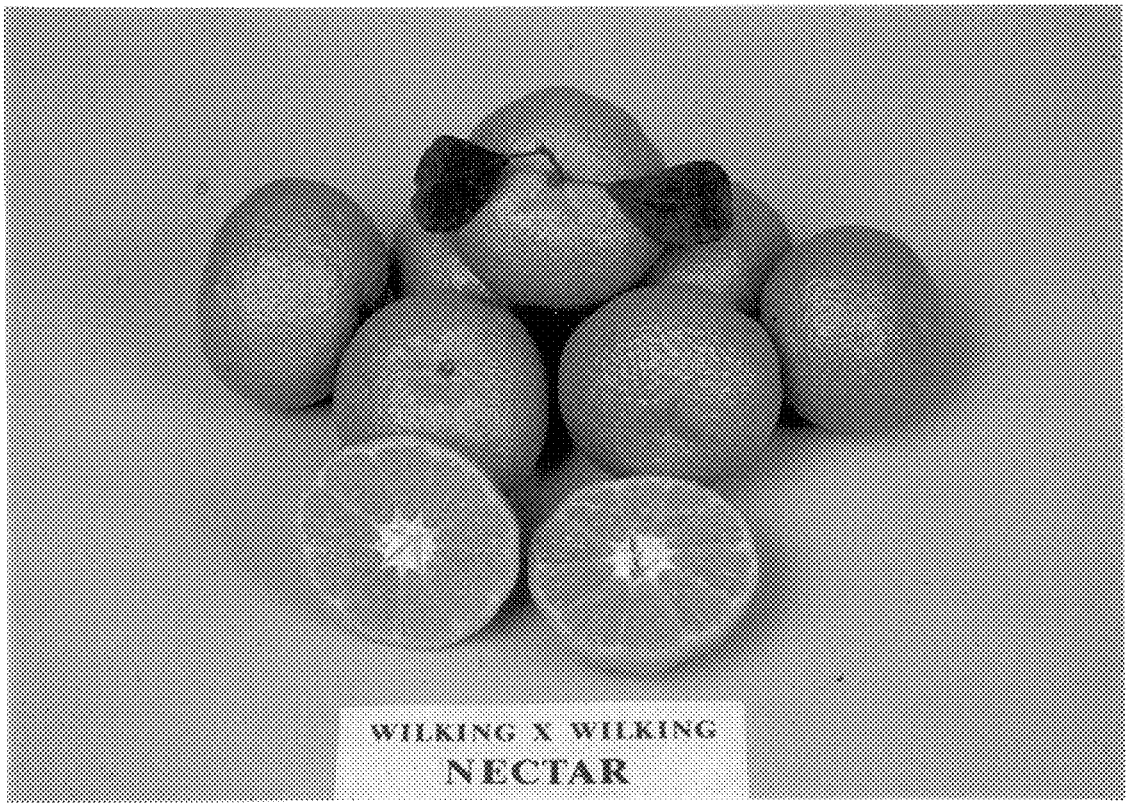
WILKING X WILKING
NECTAR